United States Patent
Becker (10) Patent No.: US 10,406,028 B1
(45) Date of Patent: *Sep. 10, 2019

(54) PUNCTAL PLUG INSERTER AND METHOD (71) Applicant: Bruce B. Becker, Malibu, CA (US)

(72) Inventor: Bruce B. Becker, Malibu, CA (US)

(*) Notice: Subject to any disclaimer, the term of this patent is extended or adjusted under 35 U.S.C. 154(b) by 518 days.

This patent is subject to a terminal disclaimer.

(21) Appl. No.: 14/664,604

(22) Filed: Mar. 20, 2015

Related U.S. Application Data (63) Continuation-in-part of application No. 13/186,665, filed on Jul. 20, 2011, now Pat. No. 9,254,225.

(51) Int. Cl.
*A61F 9/00* (2006.01)
*A61F 9/007* (2006.01)
*A61B 17/12* (2006.01)

(52) U.S. Cl.
CPC .... *A61F 9/00772* (2013.01); *A61B 17/12031* (2013.01); *A61B 17/12159* (2013.01); *A61B 2017/12054* (2013.01)

(58) Field of Classification Search
CPC .......................... A61F 9/00772; A61F 9/00781
See application file for complete search history.

(56) References Cited

U.S. PATENT DOCUMENTS

| | | | | |
|---|---|---|---|---|
| 3,949,750 A | * | 4/1976 | Freeman | A61F 9/0017 424/427 |
| 6,344,047 B1 | * | 2/2002 | Price | A61F 9/00772 604/298 |
| 9,254,225 B2 | * | 2/2016 | Becker | A61F 9/00772 |
| 2005/0154399 A1 | * | 7/2005 | Weber | A61F 2/167 606/107 |
| 2011/0196317 A1 | * | 8/2011 | Lust | A61B 50/30 604/290 |

* cited by examiner

*Primary Examiner* — Benjamin J Klein
(74) *Attorney, Agent, or Firm* — Charmasson, Buchaca & Leach, LLP

(57) ABSTRACT

A surgical tool for inserting a spile or plug into the punctal opening of a meatus such as a lacrimo-nasal canaliculus comprises an oblong, hollowed member shaped and dimensioned to be conveniently manipulated with one hand and having at one end a punctal opening and meatus-dilating shaft and, at the opposite end, a plug inserter. The dilating shaft has a cross-diameter substantially equal to the cross-diameter of the plug and is terminated by a conical spike. The inserter comprises a tip extending axially from the member and having, at its distal end, a cup whose internal geometry is commensurate with a cap at the proximal end of the plug. A penetration-resisting bearing surface is provided by the cup rim. A notch through the cup wall improves visualization of the plug during insertion. A steel wire running through the inserter has its distal end inserted into the cap of the plug. The wire can be axially withdrawn by unidirectionally pressing a button in order to release the plug after insertion into the meatus. The plug can be allowed to retract within the cup under the force of insertion or through retraction of the wire.

39 Claims, 10 Drawing Sheets

PUNCTAL PLUG INSERTER AND METHOD

PRIOR APPLICATION

This is a continuation-in-part of U.S. patent application Ser. No. 13/186,665, filed 2011 Jul. 20, incorporated herein by reference.

FIELD OF THE INVENTION

This invention relates to surgical implements and more specifically to instruments used in the treatment and repair of meati, particularly naso-lacrimal canaliculi and puncta.

BACKGROUND

Dry eye syndrome which usually results from inadequate production of the aqueous layer of tears can often be palliated by obstructing the punctum that drain tears into the nose. This is done by means of minuscule punctal spiles or plugs. Each plug features a distal glanduliform or barbed head. The head acts as an anchor and is backed by a short median shank of a cross-diameter substantially smaller than the largest portion of the head, and a broad circular cap which remains outside the punctum and can be seized with tweezers or pincers to extract the plug. The largest cross-diameter of the head must be slightly larger than the cross-diameter of the canaliculus and its opening punctum in order to maintain the plug in its optimal position.

The prior art offers an ophthalmic punctal opening dilatation and plug insertion tool available under the name Ready-Set Punctum Plug from FCI Opthalmics of Marshfield Hills, Mass. which consists of a pencil dimensioned member having at one end a dilating reamer and at the opposite end a thin shaft through which runs a small axially translatable rod. The distal extremity of the rod protrudes slightly from the end of the shaft and is sized to penetrate a small axial bore in the proximal face of the cap and thus hold the plug during its insertion into the punctal opening of a canaliculus or other type of meatus. A bi-directional squeeze mechanism in the median portion of the tool withdraws the rod and releases the plug once it has reached the desired position.

The prior art tool suffers from several critical drawbacks.

First, the dilating reamer is constituted by circular shaft of a substantial cross-diameter terminated by an elongated conical spike. The degree of penetration of the spike into a meatus determines the amount of obtained dilation. Although such a dilator has the flexibility of providing an adjustable amount of dilatation, the physician can only estimate how far to push the dilator into the punctal opening. If the dilatation is not sufficient, the insertion of the plug may be painfully difficult or impossible. If the dilatation exceeds the diameter of the cap, the plug may be inadvertently pushed too far into the canaliculus. If the dilatation even exceeds the largest diameter of the anchoring head, the plug may be too loose and soon exit the meatus.

Second, because of the relatively large forces typically required to insert the typically tight-fitting plug, it can be difficult for the physician to judge whether the plug is located at the proper optimum depth with respect to the punctum. Plugs which have been inserted too deeply can be difficult to remove, leading to tissue damage, infections or other complications.

Third, the prior art bi-directional squeeze mechanism for retracting the rod is located on a part of the tool that the physician will typically need to grasp during insertion. Therefore, when the physician grasps this portion and applies force to the tool to insert the plug through the punctum, it is possible for the physician to inadvertently actuate the squeeze mechanism and prematurely release, or partially dislodge the plug from the tool. Further, because the squeeze mechanism typically requires that the physician's thumb and index finger be located on opposite sides of the mechanism in order to actuate withdrawal of the rod, control of the tool, especially under force is made difficult.

In addition, the precarious holding of the plug by the small amount of the rod that penetrates the cap may not allow the physician much freedom of action during the insertion process, and often results in the inadvertent, premature separation of the sterile plug from the tool. The plug may be dropped before insertion or left only partially inserted. In the latter instance, another tool must be used to extract the partially inserted plug and re-attach it to the insertion tip in order to attempt a repeat of the insertion procedure. Such procedures can be difficult and time-consuming.

Lastly, many surgeons prefer to maximize visualization of the plug during insertion to the extent possible. Devices which seek to stabilize the plug while it is attached to the inserter can tend to obscure the view of the plug. This can lead to an undesirable tradeoff between stability and visibility.

Therefore, there is a need for a punctal plug insertion device and method which addresses one or more of the above problems.

SUMMARY

The principal and secondary objects of the invention are to provide improved treatment of meati.

These and other objects are achieved by an inserter tool having greater controllability. In some embodiments there is provided a tool which overcomes the above-described shortcomings by providing an improved ophthalmic instrument for dilating a punctum and safely and accurately inserting a plug, in which the cross-diameter of the meatus-dilating shaft is calibrated to the desired size. In some embodiments there is provided a tool having a cup having an internal geometry commensurate with the external shape and size of the cap is axially mounted at the end of the plug inserting shaft for securely holding and directing the plug during the insertion procedure.

In some embodiments there is provided that in a surgical tool for inserting a plug into the punctal opening of a meatus having a given diameter, wherein said plug comprises a body elongated along a first elongation axis, said body having a distal insertable portion, and a proximal cap having a distal flange surface oriented to rest against tissue surrounding said opening when properly inserted, an improvement which comprises: a median member having a proximal portion, a distal portion, and an elongated tip projecting from said distal portion; a holder for releasably securing said plug to said tip; and, an insertion-resisting bearing surface located at an axial position coplanar with or distal to said flange surface when said plug is properly positioned within said meatus.

In some embodiments said holder comprises: a radial prominence supporting said bearing surface axially spaced distally apart from said tip; and, at least one radial notch angularly adjacent to said radial prominence.

In some embodiments said at least one radial notch extends axially a first axial length.

In some embodiments said at least one radial notch extends angularly a first angle.

In some embodiments said at least one radial notch extends distally to an extent to form an angular discontinuity in said bearing surface.

In some embodiments said at least one radial notch has an outer opening larger than an inner opening.

In some embodiments said at least one radial notch is shaped and dimensioned to have a first angular dimension at a first axial location and a second angular dimension at a second axial location.

In some embodiments the tool further comprises a pane of translucent material covering a portion of said notch.

In some embodiments said portion includes an entire angular and axial dimension of said notch.

In some embodiments said elongated tip projects along said first elongation axis along which the plug is ejected from the cup.

In some embodiments said cup has an insertion axis.

In some embodiments said insertion axis is oriented at an acute angle to said first elongation axis during insertion of said plug into said meatus.

In some embodiments said acute angle is between 0 and 45 degrees.

In some embodiments said holder comprises: a cup terminating said tip and being axially aligned with said tip; and wherein said cup has an internal geometry diametrically commensurate with said cap.

In some embodiments said cup is made from a resiliently flexible, translucent material.

In some embodiments said cup is removably securable to said tip.

In some embodiments said cap is spaced an axial distance apart from said cup.

In some embodiments said axial distance is eliminated when said plug is placed under a given axial mechanical load.

In some embodiments said insertable portion has a largest cross-diameter slightly larger than said given diameter; wherein said plug has an axial bore; and wherein said tool further comprises a rod running axially within said tip and cup and having a distal extremity removably insertable into said bore.

In some embodiments said tool further comprises a unidirectionally activated withdrawing mechanism housed in a cavity within said member; wherein said withdrawing mechanism is configured to manually cause withdrawal of said distal extremity from said cup.

In some embodiments said cap is spaced an axial distance apart from said cup; and wherein said axial distance is eliminated when said withdrawing mechanism activated.

In some embodiments said withdrawing mechanism comprises: a movable beam within said cavity; a pushbutton acting upon said beam; and said rod having a proximal extremity secured to said beam.

In some embodiments said movable beam comprises a radially deflectable portion.

In some embodiments said movable beam comprises an axially translatable portion.

In some embodiments said beam is resiliently deflectable and said rod is resiliently deformable.

In some embodiments said rod is permanently deformable.

In some embodiments said tool further comprises a radial slot extending axially along said median member, wherein said slot is shaped and dimensioned to allow for said rod to form a radial bow within said slot when said rod is placed under a given axial mechanical compression load.

In some embodiments a distal extremity of said rod retracts axially under a given axial mechanical compression load.

In some embodiments there is provided a method for seating a plug in the punctum of a patient, wherein said plug has a proximal cap having a flange surface for resting against the tissue surrounding said punctum, said method comprises: selecting an oblong inserter tool having a first end releasably carrying a punctal plug thereon, and a penetration-preventing bearing surface; pushing said tool axially until a contact is made between said bearing surface and a portion of tissue surrounding said punctum; detecting an increase in resistance to further axial pushing while said contact is maintained; stopping further axial pushing in response to said detecting; releasing said plug from said tool; and, axially pulling said tool away from said plug.

In some embodiments said releasing comprises axially retracting a deformable rod from an axial bore in said plug.

In some embodiments the method further comprises prior to said pushing, inserting a pre-sized dilator located on said tool into said punctum, wherein said dilator is dimensioned according to one of a plural number of sizes for said plug.

In some embodiments the method further comprises: carrying said plug where said flange surface is located in a first position an axial distance apart from said bearing surface; and wherein said pushing comprises: allowing said cap to retract proximally when said plug is placed under a given axial mechanical load, so that said axial distance is eliminated and said flange surface is located substantially coplanar with said bearing surface.

In some embodiments the method further comprises: carrying said plug where said flange surface is located in a first position an axial distance apart from said bearing surface; and wherein said pushing comprises: axially retracting a deformable rod from an axial bore in said plug thereby allowing said cap to retract proximally, so that said axial distance is eliminated and said flange surface is located substantially coplanar with said bearing surface.

In some embodiments there is provided the combination of a punctal plug and a tool for inserting said plug into the punctal opening of a meatus; wherein said plug comprises: a body elongated along a first axis; a distal insertable portion; a proximal cap having a distal flange surface oriented to rest against tissue surrounding said opening when said plug is properly emplaced in said meatus; and, wherein said tool comprises: a median member having a proximal portion, a distal portion, and an elongated tip projecting from said distal portion; a holder for releasably securing said plug to said tip; an insertion-resisting bearing surface located at an axial position to resist penetration of said flange surface through said punctum.

In some embodiments said bearing surface and said flange surface are substantially coplanar.

In some embodiments said holder comprises: a cup terminating said tip and being axially aligned with said tip; and wherein said cup has an internal geometry commensurate with said cap.

In some embodiments said bearing surface continuously surrounds said flange surface.

In some embodiments said cap is retractably secured to said holder between an extended position and a retracted position and wherein axial position is substantially coplanar with said distal flange surface when said cap is in said retracted position.

In some embodiments said combination further comprises: said cup comprising a radial prominence supporting said bearing surface; and, at least one radial notch angularly adjacent to said support structure.

In some embodiments said at least one radial notch extends axially a first axial length.

In some embodiments said at least one radial notch extends angularly a first angle.

In some embodiments said at least one radial notch extends distally to an extent to interrupt an angular gap in said bearing surface.

In some embodiments the tool further comprises a punctum and meatus dilator projecting axially from an end of said member opposite said tip, wherein said dilator is dimensioned according to one of a plural number of sizes for said plug.

In some embodiments said dilator comprises: a cylindrical stem having a cross-diameter substantially equal to the cross-diameter of said insertable portion; and a conical spike terminating said stem.

In some embodiments there is provided that in a surgical tool for inserting a plug into the opening punctum of a meatus, an improvement which comprises a cylindrical stem having a cross-diameter commensurate with said plug and a conical spike terminating said stem.

In some embodiments there is provided that in a surgical tool for inserting a plug into the opening punctum of a meatus, wherein said plug includes a cap at a proximal end having a distal flange surface oriented to rest against tissue surrounding said opening, an improvement which comprises: a holder for releasably securing said plug to said tool; and, an insertion-resisting bearing surface located at an axial position commensurate with or distal to said flange surface when said plug is properly positioned within said meatus.

In some embodiments the cap of said plug has a central, axial bore in a proximal face of said cap, and said tool further includes an axial rod extending through said holder and being sized to intimately penetrate said bore, and wherein said improvement further comprises said rod having an extremity translatable in and out of said holder.

In some embodiments said holder comprises a distally open-ended cup structure made from a resiliently flexible, translucent material.

In some embodiments said cap is spaced an axial distance apart from said cup structure.

The content of the original claims is incorporated herein by reference as summarizing features in one or more exemplary embodiments.

DESCRIPTION OF THE EXEMPLARY EMBODIMENTS

Referring now to the drawing, there is shown in FIGS. 1-4 a surgical tool 11 according to an exemplary embodiment of the invention and specifically adapted to install a spile or plug 12, about 1.5 millimeters in axial length, through the punctal opening of a lacrimal canaliculus meatus 3.

Figures 1, 2, 3:
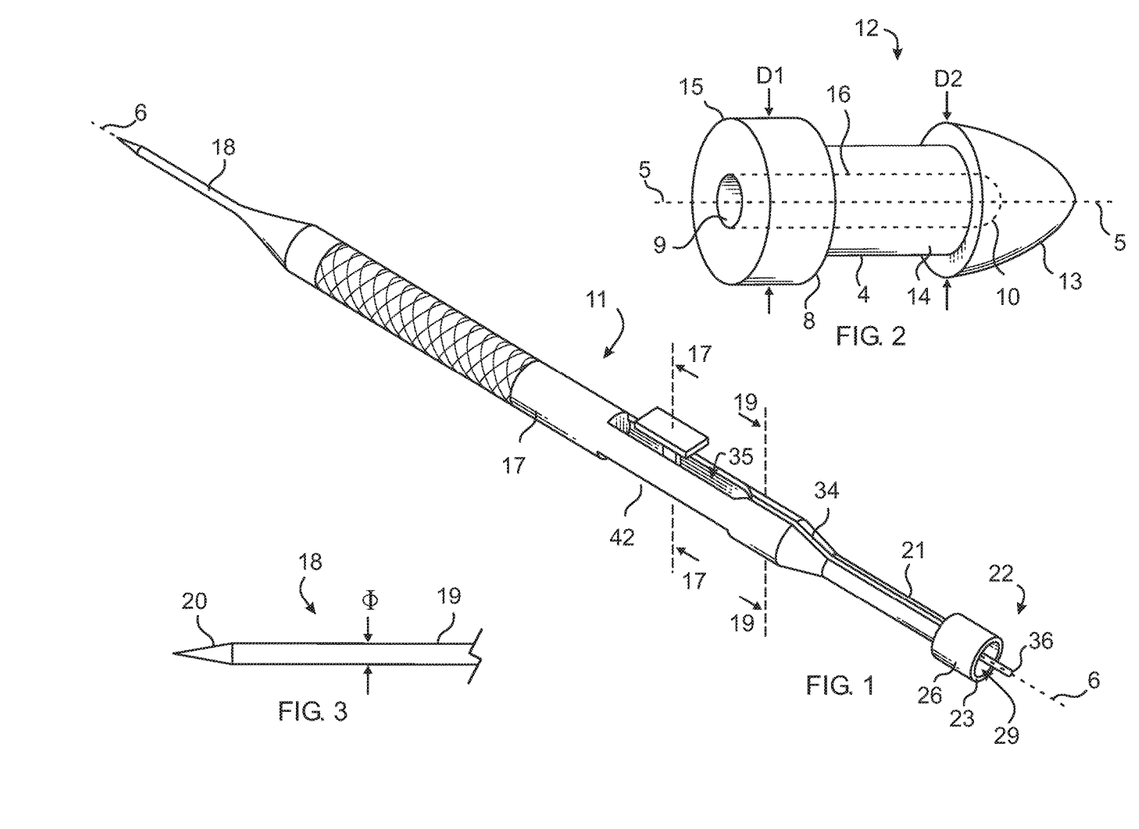
FIG. 1 is a perspective view of a plug-inserting and meatus-dilating tool according to an exemplary embodiment of the invention.
FIG. 2 is a perspective view of a plug.
FIG. 3 is a partial side view of a meatus-dilating portion of the tool.

In this example, as shown in FIG. 2, the punctal plug 12 comprises a body 4 made of a unitary piece of sterile, resiliently deformable, biocompatible material such as silicone, elongated along an elongation axis 5. The body has a distal bulb or glanduliform, in the form of a barbed head 13. The head has a largest cross-diameter D2 slightly larger than the internal cross-diameter of the host meatus in order to be frictionally retained in position therein. Thus, it can be forcefully inserted through the punctum and held securely in a canaliculus or other type of meatus. The head is backed by a narrow cylindrical shank 14 terminating in a proximal substantially cylindrical cap 15 having a cross-diameter D1 larger than the shank and typically larger than the largest cross-diameter D2 of the head.

The cap 15 therefore terminates in a distal flange surface 8 which is oriented to rest against the zone of tissue 7 surrounding the punctal opening when the plug 12 is properly emplaced in the meatus 3. A central, axial bore 16 extends through the plug from a circular opening 9 in the proximal face of the cap, through the shank 14, and terminating at a closed end 10 within the head 13. The plug 12 can be inserted through the punctal opening of a meatus with the cap 15 remaining on the outside. The plug can eventually be removed from the punctum by grabbing it with tweezers or pincers.

The meatus-dilating and plug-inserting tool 11 comprises an oblong pencil-shaped and dimensioned member 17 having a major axis 6. A punctum and meatus-dilating portion 18, as illustrated in FIG. 3, is about 20 millimeters in axial length and consists of a cylindrical stem 19 terminating into a pointed conical spike 20 which projects axially from a first, proximal portion of the member. The spike can be sharp or semi-sharp. The cross diameter 1 of the stem is calibrated to reflect the cross-diameter of desired meatus opening. The physician can thus introduce the punctum and meatus-dilating portion 18 through a punctal opening and into a meatus to size them according to the dimensions of the plug. Thus, a differently sized plug can be provided pre-loaded on a tool having an appropriately sized dilating portion for a single use. In other words, the dilator can be dimensioned according to one of a plural number of sizes for said plug. With such a pre-sized dilator, the physician can simply insert the dilator beyond the spike in order to properly dilate the punctum and meatus.

A shaft 21, about 30 millimeters long, projects axially from the opposite, distal portion of the tool member 17 and is distally terminated by a distal tip 5. The tip carries a structure 22 which both securely carries the plug 12 during insertion and provides a penetration-resisting bearing surface 23 sized, shaped, dimensioned, and located to resist and in most cases prevent over-penetration of the plug through the punctum during insertion.

Figure 4:
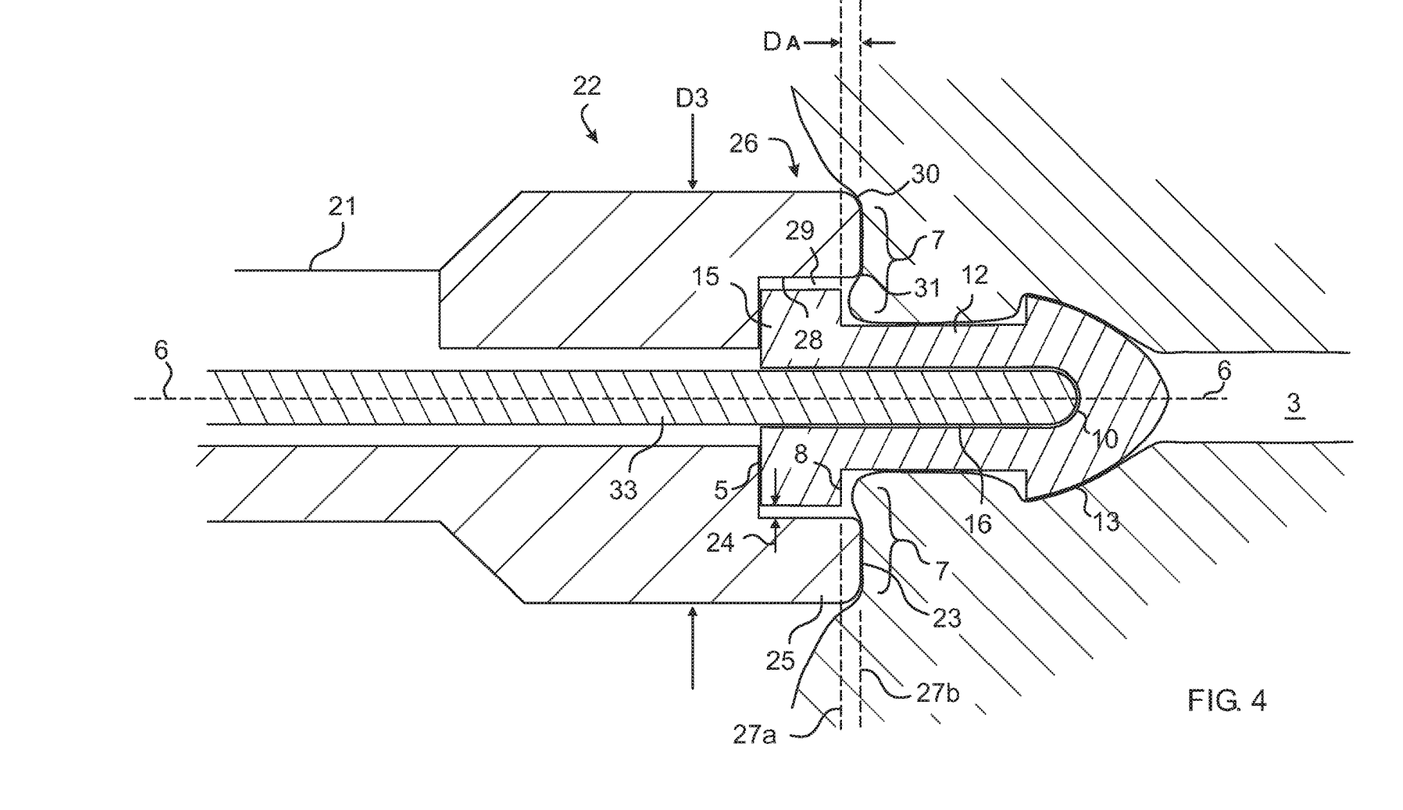
FIG. 4 is a diagrammatic partial cross-sectional side view of the tool of FIG. 1 shown during plug insertion through the punctum.

As shown in FIG. 4, the insertion-resisting bearing surface 23 is located at an axial position coplanar with or distal to the distal flange surface 8 of the plug 12 when the plug is properly positioned within the meatus so that the distal flange surface rests against a zone of tissue 7 surrounding the punctum. At this location the bearing surface contacts and bears against the zone preventing penetration of the cap 15 into the meatus 3. The bearing surface is oriented to face in substantially the distal direction which is substantially the same direction as the distal flange surface.

In other words, the bearing surface 23 can be said to be substantially adjacent to the distal flange surface 8. The word "substantially" is used because minor axial and radial separation may exist between the distal flange surface and the bearing surface when the tool is at rest and when subject to the forces of insertion as will be described in greater detail below. For example, in this embodiment a small gap 24 can be found between the radially inner extent of the bearing surface and the radially outer extent of the flange surface so that the plug can easily disengage from the structure. Further, both the distal flange surface and the bearing surface can be substantially planar and fall within planes 27a and 27b respectively. The substantially parallel planes can be separated a minor axial distance $D_A$ while remaining substantially axially and radially adjacent and substantially coplanar.

The bearing surface 23 in the present embodiment is supported by a radial prominence 25 formed in the embodiment of FIG. 4 by a distally located, distally open-ended cup structure 26. The substantially cylindrical cup 26 is oriented substantially coaxially with the major axis 6 of the shaft 21. The cup has a generally axially cylindrical wall 28 terminating a substantially circular distal rim which forms the penetration-resisting bearing surface 23 circumferentially surrounding a substantially circular distal opening to a substantially cylindrical internal cavity 29 and extending radially beyond the radial extent of the cap 15 thus leaving the small annular gap 24. Thus the cup can have an internal geometry that is substantially diametrically commensurate with the cap 15 of the plug 12.

In this embodiment, the axial location of the bearing surface 23 is selected to be slightly distal to the flange surface 8. In other words, the shape of the bearing surface is selected to be substantially planar and located within a plane 27a substantially perpendicular to the major axis 6 of the cup 26 and separated an axial distance $D_A$ from the substantially planar and substantially parallel flange surface 8. Alternately, the two surfaces can be exactly or essentially coplanar.

The diameter D3 of the cup 26 is selected to provide adequate surface area to the bearing surface 23 in order to prevent penetration of the cup through the punctum but not be so large as to obscure the view of the plug 12 during insertion. Thus, the diameter is preferably between about 1.01 and 3 times the diameter D2 of the cap 15, and more preferably between about 1.1 and 1.8 times the diameter of the cap. In this way, the forces of the bearing surface 23 against the tissues surrounding the punctum are evenly distributed during plug placement enhancing axial alignment of the plug 12 with the meatus 3.

In this embodiment, the radially distal lip 30 and the radially proximal lip 31 of the rim of the cup 26 are rounded to afford additional comfort. In this embodiment, the internal geometry of the cup is selected to substantially match the outline of the cap 15 at the proximal end of the plug. In other words, the cup is commensurate with the outline of the cap.

Figure 5:
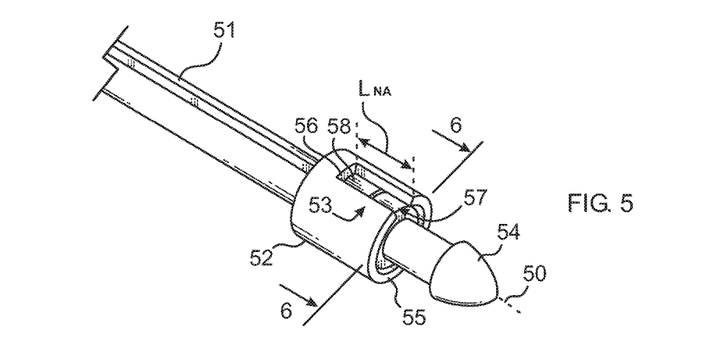
FIG. 5 is a diagrammatic partial perspective view of an alternate embodiment of the tool having a viewing notch through the cup structure.

In the embodiment of FIG. 1, the bearing surface 23 completely and continuously surrounds the distal flange surface 8. However, in order to improve visibility of the plug during insertion, interruptions in the continuity of the bearing surface can occur without departing from its penetration preventing function. For example, in FIGS. 5-6 there is shown an alternate embodiment of an inserter having a distal end of a shaft 51 having a cup structure 52 adapted to have a notch 53 which allows the physician to view a portion of the plug 54 therethrough. The notch extends an axial length $L_{NA}$ from an axially proximal terminus 56 to an axially distal terminus 57 which, when extended to the bearing surface 55, also creates an angular discontinuity or gap 57 in the bearing surface 55. The dimensions of the gap can be maximized to give greater visualization or minimized to improve the stability of the plug in the inserter and to provide a greater surface area of the bearing surface for contacting the tissues surrounding the punctum and preventing over-insertion of the plug. In this embodiment the notch is shown having a generally rectangular shape having essentially a uniform angular dimension along its axial length.

Figure 6:
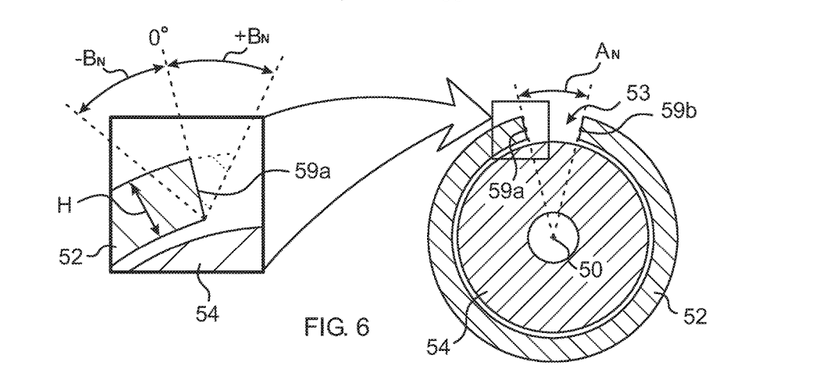
FIG. 6 is a cross-sectional end view taken along line 6-6 of FIG. 5.

As shown in FIG. 6, the notch 53 can have an angular dimension spanning over an angle $A_N$ which can range between about 10 degrees and about 330 degrees. The larger the angle is, the more visibility it provides. However, larger angles also result in less bearing surface for contacting the tissues surrounding the punctum, and potentially less stability provided to the plug during insertion. For most applications it has been found the a range of between about 45 degrees and about 180 degrees will be adequate, with an angle within plus or minus 10 degrees of about 150 degrees being found to provide the best balance. In addition one or more of the angular walls 59a,59b of the notch can be diametrically oriented to the cup. In other words, each of the walls can be located within a plane common to the central axis 50 of the cup 52 as shown thus being at a diametrically 0 degree angle. Alternately, one or more of the walls, or even part of the walls can be oriented at a non-zero angle within a range of angles between $-B_N$ and $+B_N$ with respect to the diametrical orientation. The height H of the walls are selected to provide adequate structural support to the bearing surface of the cup while maintaining a non-bulky outer dimension. For most applications, the height preferably ranges between about 0.1 millimeter and 2.0 millimeters, more preferably between about 0.2 millimeter and 1.2 millimeters in order to balance adequate support with low bulk.

Figure 7:
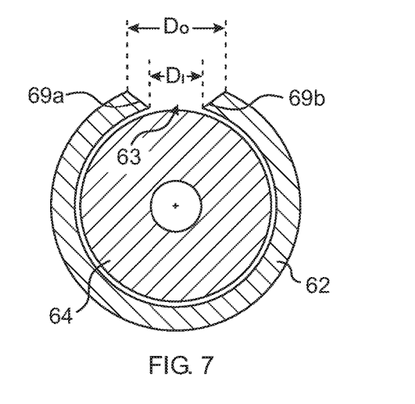
FIG. 7 is a cross-sectional end view showing an alternate notch shape.

Alternately, as shown in FIG. 7, the walls 69a,69b of the notch 63 in the cup 62 can be oriented at an angle that causes the notch to have a wider radially outward opening $D_O$ and a narrower radially inward opening $D_I$. This allows for increased viewing angles, enhancing visibility while maintaining greater contact and thus stability to the plug 64.

Figure 8:
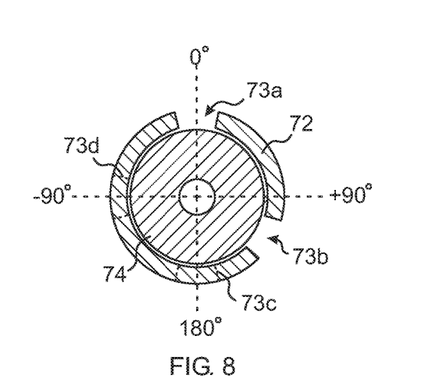
FIG. 8 is a cross-sectional end view showing alternate notch locations.

Alternately, as shown in FIG. 8, one or more notches 73a,73b can be located at various angular positions through the wall of cup structure 72 in order to better visualize the plug 74 during insertion. For example, a first notch 73a can be centered angularly at the 0 degrees or 12 o'clock position. A second notch 73b can be centered angularly at approximately the +120 degree position. Indeed, the entire circumference of the cup structure is available for locating additional notches 73c,73d for example. Of course, care must be taken to shape, dimension and locate the notches without severely disturbing the functionality of the bearing surface and plug holding structure. Another advantage is that the one or more notches can be located at other angular locations depending on the preferences of the surgeon and the procedure being conducted.

Figure 9:
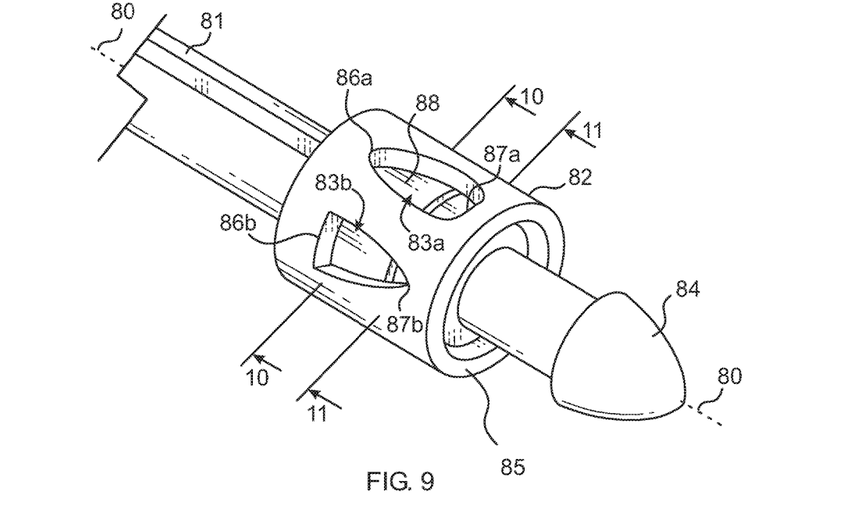
FIG. 9 is a diagrammatic partial perspective view of an alternate embodiment of the tool having a plural number of differently shaped viewing notches through the cup structure.
Figure 10:
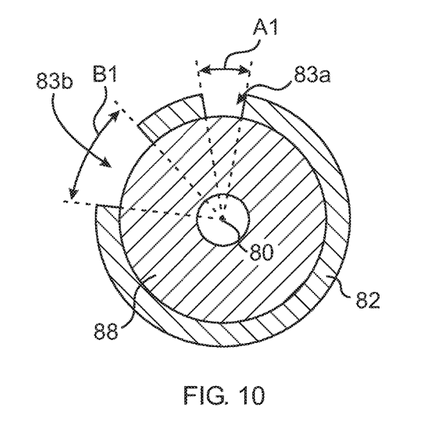
FIG. 10 is a cross-sectional end view taken along line 10-10 of FIG. 9.
Figure 11:
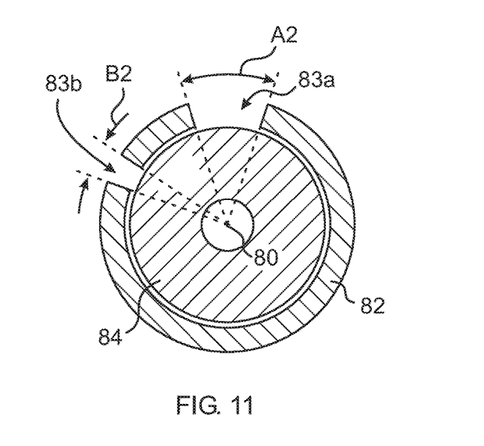
FIG. 11 is a cross-sectional end view taken along line 11-11 of FIG. 9.

FIGS. 9-11 shows that the cup structure 82 located at the tip 88 of the shaft 81 elongated along an axis 80 can have one or more notches 83a,83b that are complexly shaped having angular dimensioning which varies according to axial position depending on the desired strength and visibility characteristics. By way of example, the notch 83a is shown having an elongated egg-shape whereas the notch 83b is shown having a generally lanciform shape. The notch 83a can extend axially from a proximal terminus 86a to a distal terminus 87a and have first angular dimension A1 at a first, proximal axial location shown in FIG. 10 and a second angular dimension A2 at a second, distal axial location shown in FIG. 11. Similarly, the notch 83b can extend axially from a proximal terminus 86b to a distal terminus 87b and have first angular dimension B1 at a first, proximal axial location shown in FIG. 10 and a second angular dimension B2 at a second, distal axial location shown in FIG. 11. Thus, it can be understood that a notch 83a can have a narrower angular dimension A1 near the proximal terminus 86a and a wider angular dimension A2 near the distal terminus 87a. By varying the angular dimensioning of a notch according to axial position the tool designed can adjust the strength of the cup structure which affects stability and control of the plug during insertion, and adjust the visibility of the cap portion of the plug 84 against the tip 88 of the shaft 81. This adjustability can be especially useful when a more flexible material is used for the cup structure.

Figure 12:
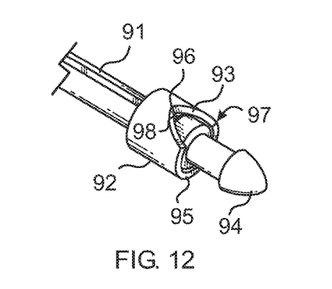
FIG. 12 is a diagrammatic partial perspective view of an alternate embodiment of the tool having a single lanciform shaped notch through the cup structure.

FIG. 12 shows that the cup structure 92 can have a single, complexly shaped notch 93 that extends in a generally lanciform manner from a narrower, rounded or pointed proximal terminus 96 to a widened distal terminus 97 interrupting the bearing surface 95 to form a gap. The notch has an axial length sufficient to reveal the tip 98 of the shaft 91 in relation to the proximal end of the cap structure of the mounted plug 94.

Figure 13:
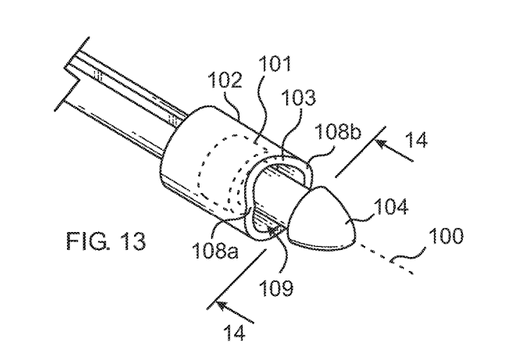
FIG. 13 is a diagrammatic partial perspective view of an alternate embodiment of the tool having a single lanciform shaped notch through the cup structure and a deeper cup internal cavity.
Figure 14:
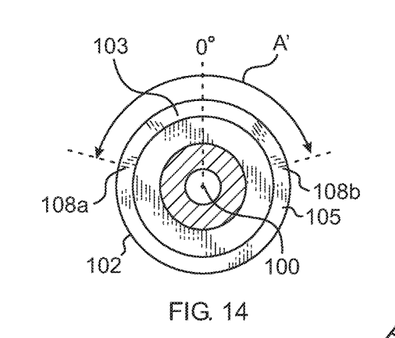
FIG. 14 is a cross-sectional end view taken along line 14-14 of FIG. 13.

FIGS. 13 and 14 show that the cup structure 102 can have a deeper internal cavity 109 so that the cap 101 of the plug 104 is fully contained within the cavity when the plug is fully seated in the inserter holder prior to insertion. In this embodiment a notch 103 has an axial length which is short enough so that the view of the cap is obscured until the plug starts to be extracted from the cup structure. In this way, the cup structure provides improved stability against forces having a component off the axis 100 of the plug. In addition, the transitions 108a,108b between the notch and the bearing surface 105 can be rounded to enhance comfort and better avoid minor damage to the tissues contacted. Of course, the use of one or more notches can provide greater visibility of the plug and/or tip prior to and/or during insertion.

Figure 15:
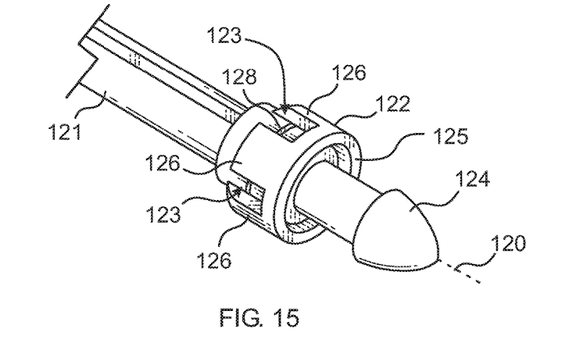
FIG. 15 is a diagrammatic partial perspective view of an alternate embodiment of the tool having a spaced apart prong supported cup structure.

FIG. 15 shows that the cup structure 122 can have a continuous, planar, ring-shaped bearing surface 125 supported coaxially with the axis 120 of the mounted plug 124 by one or more radial prominences in the form axially and radially extending prongs 126 separated by an equal number of angularly adjacent notches 123. Each prong connects the distal part of the cup structure forming the bearing surface with the shaft 121 near its distal tip 128. This embodiment maximizes the angular coverage of the bearing surface while providing visualization of the plug cap in it fully engaged position on the inserter tool.

Referring now to FIGS. 16-20, there is shown an alternate embodiment of a punctal plug insertion tool including a thin rod 33 in the form of a resiliently flexible steel wire runs from a cup structure 26 within a slot 34 to a cavity 35 in a median part of the tool member 17. The distal extremity 36 of the rod is sized to intimately penetrate the bore 16, about 0.25 millimeter in diameter, in the plug 12 and, in this embodiment, hold the cap 15 within the cup and the whole plug at the distal end of the shaft 21 during the insertion process.

Figure 16:
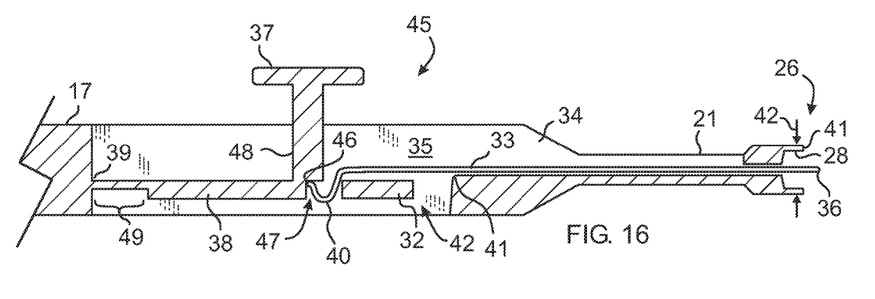
FIG. 16 is a diagrammatic partial cross-sectional side view of the tool of FIG. 1 shown in the plug-holding position.
Figure 17:
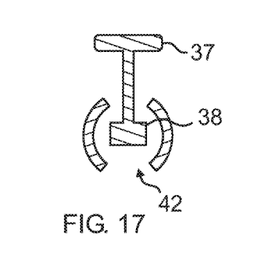
FIG. 17 is a cross-sectional view taken along line 17-17 of FIG. 1.
Figures 18, 19:
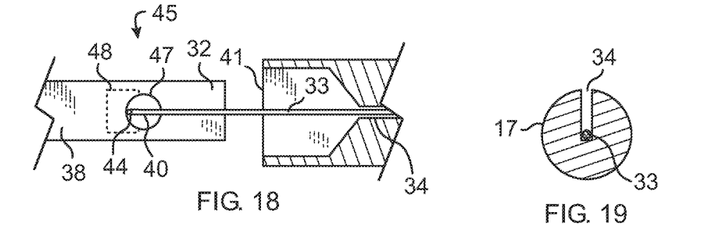
FIG. 18 is a diagrammatic partial cross-sectional top view of the tool of FIG. 1 showing the rod engaging the deflectable beam.
FIG. 19 is a cross-sectional view taken along line 19-19 of FIG. 1.
Figure 20:
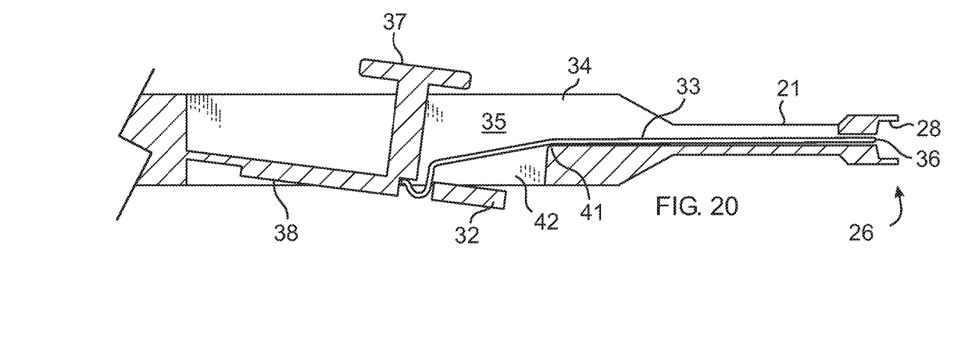
FIG. 20 is a diagrammatic partial cross-sectional side view of the tool of FIG. 1 shown in the plug-releasing position.

A uni-directionally activated rod-withdrawing mechanism 45 housed in the cavity 35 and activated by a pushbutton 37 translates the rod 33 from its plug-holding position shown in FIG. 16 to a plug-disengaged, plug-releasing position shown in FIG. 20. The mechanism consists of the pushbutton acting on a deflectable beam 38 fixedly secured at one end 39 to the core of the tool member 17 and tied at its other distal end 32 to the proximal extremity of the rod. The proximal extremity of the rod is formed into an upturned hook structure 40 which dips through a vertical hole 47 formed through the beam. The hole is partially overlapped by a portion of the pushbutton post 48 where it connects to the beam. This creates a crook 46 which is engaged by the proximal tip 44 of the hook structure. This structure provides an easily assembled anchorment between the proximal extremity of the rod and the beam. The beam can have a thinned portion 49 near the end 39 secured to the tool to adjust the force necessary to cause deflection.

In one embodiment the beam 38 can be resiliently deflectable and the rod 33 resiliently deformable so that when the button 37 is released, the beam resiliently returns to its un-deflected state and the rod returns to its un-deformed state. In this way, the release of the button can cause the distal extremity 36 of the rod to re-engage into the axial bore 16 of the plug 12 and allow the physician to reposition the plug if desired. Alternately, the rod can be substantially permanently deformable so that release of the button does not cause the distal extremity to re-extend distally toward the plug. In this way, there is no chance that the distal extremity of the rod will re-engage the bore 16 in the plug.

As shown in FIG. 20, when the pushbutton 37 is depressed, the beam 38 deflects and pulls the rod 33 against the shoulder 41 at the intersection of the slot 34 and cavity 35 causing the rod to slightly translate proximally out of the cup 26 and thus the cap 15 allowing the plug 12 to be released from the cup. A cutout 42 in the wall of the cavity opposite the pushbutton provides clearance for the downward movement of the distal end 32 of the beam.

The plug can thus be conveniently mounted at the distal end of the shaft 21 and have its cap 15 held into the cup 26 by the distal extremity 36 of the rod 33. The physician can then insert the plug up to, but exclusively of the cap into the punctal opening of a meatus. Pressing the pushbutton 37 liberates the plug 12 from the tip and allows for the withdrawal of the tool.

Referring now to FIGS. 21-24, there is shown an alternate embodiment of a punctal plug insertion tool 130 including a thin rod 133 in the form of a resiliently flexible steel wire runs from a cup structure 226 within a slot 134 to a cavity 135 in a median part of the tool member 137. The distal extremity 136 of the rod is sized to intimately penetrate the bore 16, about 0.25 millimeter in diameter, in the plug 12 of FIG. 2 and, in this embodiment, hold the cap 15 within the cup and the whole plug at the distal end of the shaft 221 during the insertion process.

Figure 21:
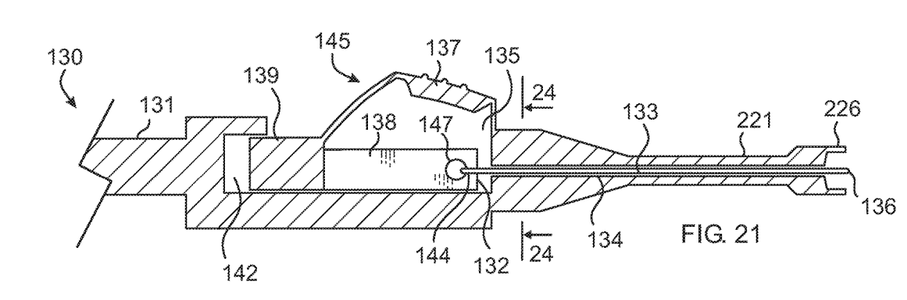
FIG. 21 is a diagrammatic partial cross-sectional side view of an alternate embodiment of the rod retraction mechanism shown in the plug-holding position.
Figure 22:
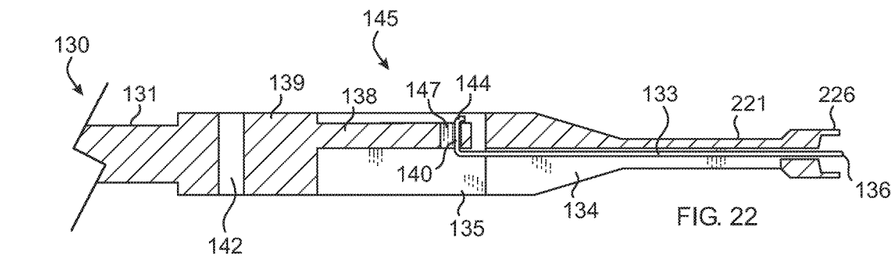
FIG. 22 is a diagrammatic partial cross-sectional top view of tool of FIG. 21.
Figure 23:
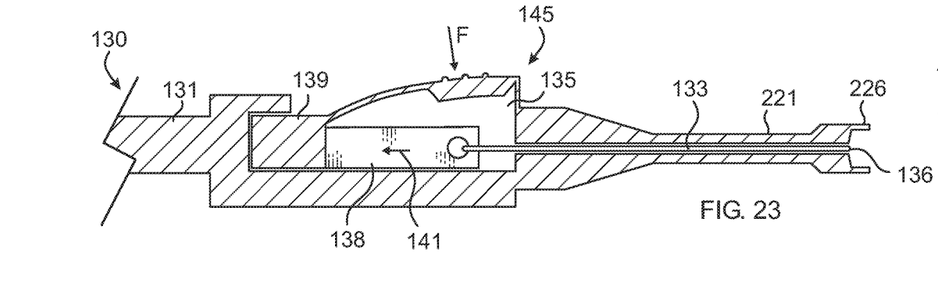
FIG. 23 is a diagrammatic partial cross-sectional side view of the tool of FIG. 21 shown in the plug-releasing position.
Figure 24:
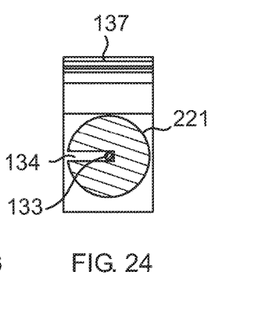
FIG. 24 is a cross-sectional view taken along line 24-24 of FIG. 21.

A uni-directionally activated rod-withdrawing mechanism 145 housed in the cavity 135 and activated by a pushbutton 137 translates the rod 133 from its plug-holding position shown in FIG. 21 to a plug-disengaged, plug-releasing position shown in FIG. 23. The mechanism consists of the pushbutton hingedly connected to the tool member 131 and acting on a translatable beam 138 slidingly secured at a proximal end 139 to the core of the tool member 131 and tied at its other distal end 132 to the proximal extremity 144 of the rod. The proximal extremity of the rod is formed into a hook structure 140 which dips through and engages a hole 147 formed through the beam.

In this embodiment the beam 138 can be resiliently axially translatable so that when the button 137 is released, the beam resiliently returns to its un-translated state. In this way, the release of the button can cause the distal extremity 136 of the rod to re-engage into the axial bore 16 of the plug 12 and allow the physician to reposition the plug if desired. Alternately, the button can remain depressed after the button is release so that the rod remains permanently withdrawn.

As shown in FIG. 23, when the pushbutton 137 is depressed by a substantially radial force F, the beam 138 translates axially in the proximal direction 141 and pulls the rod 133 out of the cup 226 and thus the cap 15 allowing the plug 12 to be released from the cup. A receptacle 142 at the proximal end of the cavity provides clearance for the rearward movement of the proximal end 139 of the beam.

The plug can thus be conveniently mounted at the distal end of the shaft 221 and have its cap 15 held into the cup 226 by the distal extremity 136 of the rod 133. The physician can then insert the plug up to, but exclusively of the cap into the punctal opening of a meatus. Pressing the pushbutton 137 liberates the plug 12 from the tip and allows for the withdrawal of the tool.

Figure 25:
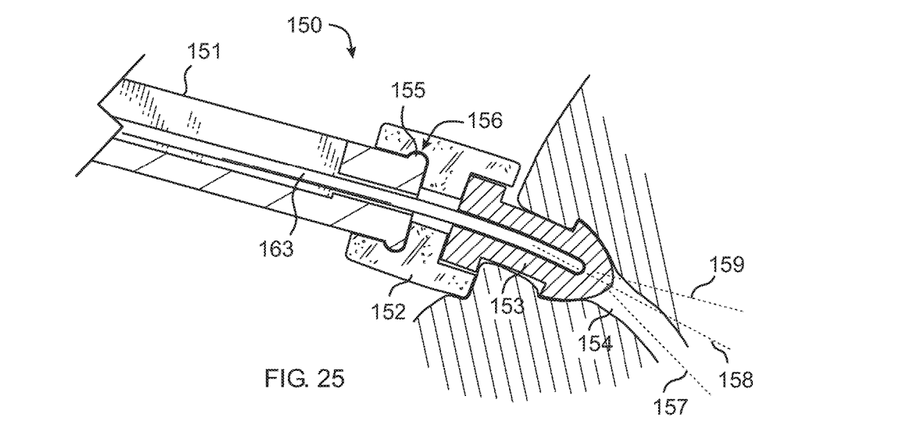
FIG. 25 is a diagrammatic partial cross-sectional side view of an alternate embodiment of the tool having a resiliently deformable plug-carrying structure.

Referring now to FIG. 25, there is shown an alternate embodiment of the tool 150 having a distally projecting shaft 151. A cup 152 made from a resiliently deformable material such as silicone, polyurethane, Teflon brand material, ethylene, or propylene is mounted to the distal end of the shaft. In addition, the cup material can be sterile, biocompatible, and translucent. The mounting of the cup to the shaft can be made more robust by a circumferential bead 155 engaging a corresponding circumferential groove 156 in the cup. The cup material can allow the cup to be removably secured to the distal end of the shaft. Optionally, a layer of adhesive can be used between some of the surfaces of the shaft contacting the cup to more securely bond the cup to the shaft.

The cup 152 being made from a resiliently deformable material allows for enhanced comfort during placement of the plug through the patient's punctum. It also allows the major elongation axis 158 of the plug 153 to deflect toward the axis 157 of the meatus 154 when the major insertion axis 159 of the tool is angularly misaligned with the meatus. It shall be noted that the rod 163 can be dimensioned to allow for the flexible deflection of the rod and plug. This deflectability allows for a more rapid, comfortable, and accurate insertion. The cup being made from a translucent material allows the physician to better view the plug and punctum during emplacement.

Figure 26:
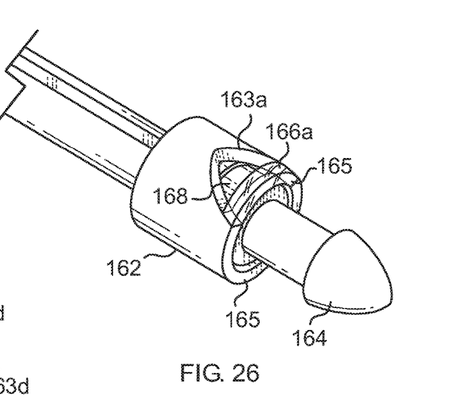
FIG. 26 is a diagrammatic partial perspective view of an alternate embodiment of the tool having a pane of translucent material partially covering a notch through the cup structure.

FIG. 26 shows that the cup structure 162 can have at least one notch 163a that is at least partially covered by a pane 166a of translucent material such as transparent rigid plastic. The embodiment of FIG. 26 further shows that the pane 166a can be shaped, dimensioned and located to cover the most distal portion of the notch 163a so that it provides a continuation of the bearing surface 165 so that it entirely surrounds the distal opening of the cup through which the plug 164 distally extends. The open proximal portion of the notch not being covered by the pane allows open viewing of the cap 168 of the plug therethrough. By covering a portion of the notch with translucent material, the strength of the cup structure and the stability provided to the plug during insertion can be enhanced while maintaining enhanced visibility. Also, the pane can be used to enhance the bearing surface provided by the cup lip while maintaining enhanced visibility.

Figure 27:
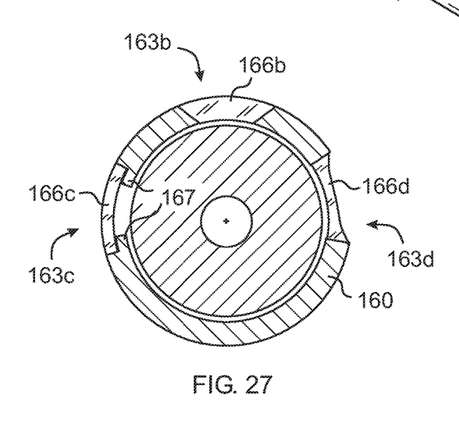
FIG. 27 is a diagrammatic cross-sectional view of an alternate embodiment of the tool having panes of translucent material partially covering a notches through the cup structure.

FIG. 27 shows that for any of the embodiments, the cup structure 160 can have one or more notches 163b,163c,163d that are at least partially or fully covered by a pane 166b, 166c,166d of translucent material such as transparent plastic. For example notch 163b can be shaped and dimensioned similarly to the notch of FIG. 7 and be completely covered by the pane 166b. In other words, the portion of the notch 163b covered by the pane 166b includes the entire angular, axial, and radial dimensions of the notch. Notch 163c shows that the notch walls can have flanges 167 so that a reduced thickness pane 166c can cover the entire angular and axial dimensions of the radially outward portion of the notch. Notch 163d shows that the pane 166d can seal the notch without covering a portion that includes the entire outer angular dimension of the notch by not filling the entire radial dimension of the notch.

Figure 28:
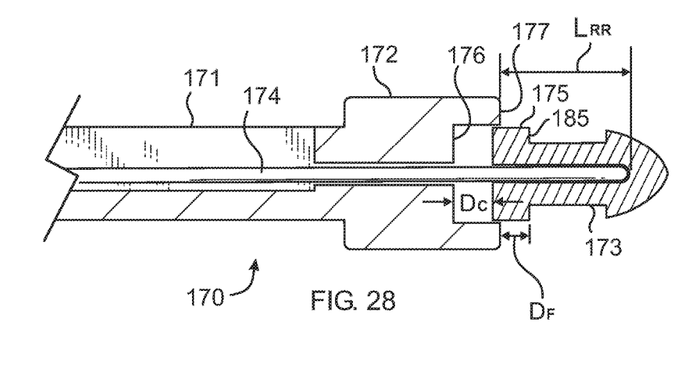
FIG. 28 is a diagrammatic partial cross-sectional side view of an alternate embodiment of the tool having a retractably carried plug in a mechanically unloaded condition.
Figure 29:
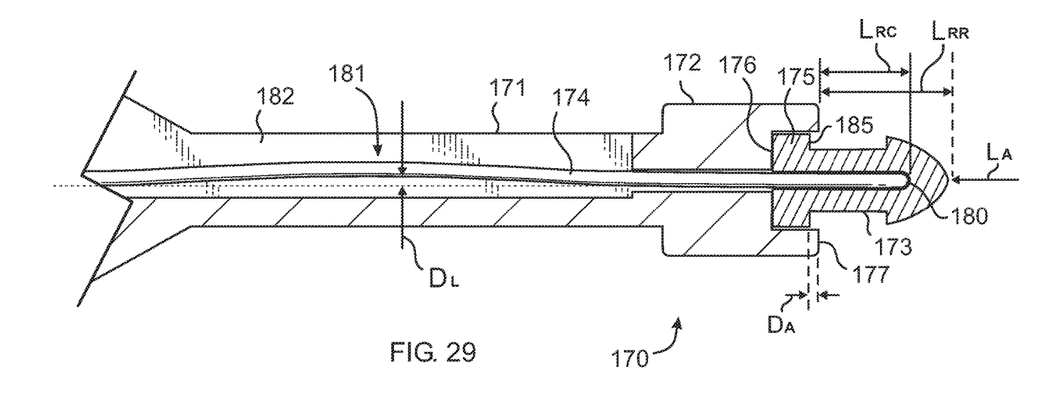
FIG. 29 is a diagrammatic partial cross-sectional side view of the tool of FIG. 28 while under a given axial mechanical load.

Referring now to FIGS. 28-29, there is shown an alternate embodiment of the tool 170 having a distally projecting shaft 171 supporting a coaxially oriented distal cup structure 172 for carrying and orienting a punctal plug 173. In this embodiment the plug is carried distally further out on the tool so that the physician can better see the plug during insertion.

As shown in FIG. 28, when the plug 173 is fully engaged upon the retractable rod 174 and while the plug and rod are at rest under no applied axial mechanical load, the plug is located in a distally extended position where its cap 175 is spaced apart an axial distance $D_C$ from the proximal floor 176 of the cup. Consequently, the flange surface 185 of the cap is located a distance $D_E$ from the distal rim 177 of the cup which forms the penetration-resisting bearing surface. In this "at rest" position the rod 174 extends distally beyond the distal rim 177 of the cup by an axial length $L_{RR}$.

As shown in FIG. 29, during installation of the plug into the meatus, an external mechanical load is applied. An axial component $L_A$ of that load can cause the distal extremity 180 of the rod 174 to retract slightly proximally, thus causing the rod to form a bow 181 in the slot 182 of the tool. In other words, the flexibility of the rod is selected to allow for the bow of the rod to deflect radially a distance DL within the slot when placed under an axial compression load. The load on the rod occurs when the plug is inserted in the meatus and the flange surface 185 of the plug 173 contacts the tissue surrounding the punctum and the resistence to further insertion increases. It is important to note that the mechanical properties of the rod and the plug must be selected to prevent penetration of the cap of the plug through the punctum. In other words the rod cannot be so stiff that is fails to retract slightly under the insertion force when the flange comes into contact with the tissue surrounding the punctum. Alternately, the physician can activate a rod-withdrawing mechanism such as the pushbutton 37,137 according to previous embodiments to retract the rod and allow the plug to seat completely within the cup prior to or while the plug is being pushed into the meatus. In this way, if the distal end of the plug is bent by non-axial forces or the rod does not retract automatically, the rod will not interfere with proper placement of the plug.

It shall be noted that the bowing of the rod 174 will cause the cap 175 of the plug to travel proximally so that it retracts within the internal cavity of the cup structure 172 until the proximal surface of the cap bears against the proximal floor 176 of the of the cup. The distal flange surface 185 of the plug will then be substantially coplanar with the distal rim 177 of the cup, thus acting as the penetration-resisting bearing surface as described above in connection with an earlier embodiment. This helps prevent further insertion of the plug into the meatus. Similarly to a previous embodiment, the word "substantially" is used because the distal flange surface 185 may be located a minor axial distance $D_A$ from the bearing surface 177.

Selecting the rod 174 to have a certain rigidity allows the physician to gauge how much axial force is being applied, by detecting whether and to what extent the rod has begun to bow and the plug has begun to retract, thereby providing feedback to the physician. For most typical punctal plug installation applications the rod can be selected to be between about 0.1 millimeter and 0.4 millimeter in diameter to allow for retraction during application of the maximum axial force during insertion.

Figure 30:
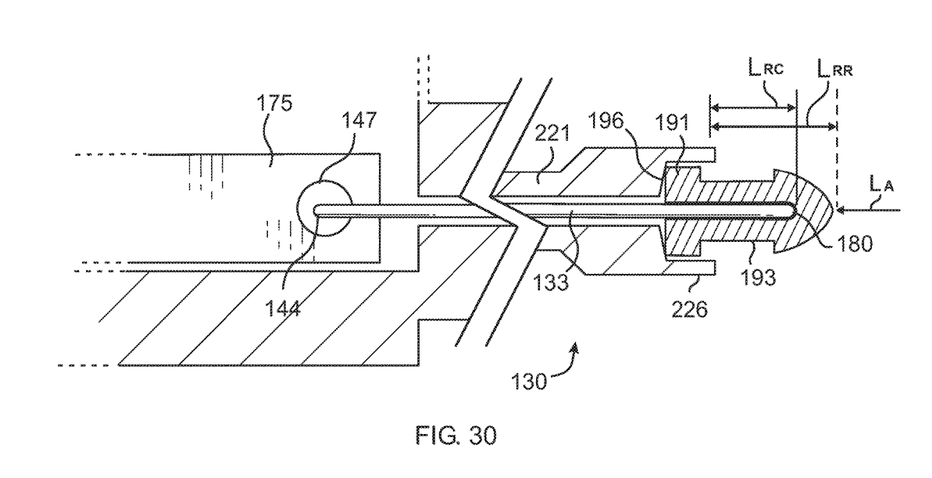
FIG. 30 is a diagrammatic partial cross-sectional side view of the tool of FIG. 21 while under a given axial mechanical load.

Similarly, as shown in FIG. 30, the tool of the embodiment of FIG. 21 can accommodate an axial component load $L_A$ which pushes a plug 193 proximally into the cup 226 until the proximal cap rests against the tip 196 of the shaft 221 which causes the rod 133 to retract slightly proximally, thus causing the proximal end 144 of the rod to move proximally with respect to hole 147 in the beam 138. Alternately, the physician can activate the pushbutton 137 to retract the rod and allow the plug to seat completely within the cup prior to or while the plug is being pushed into the meatus. In this way, if the distal end of the plug is bent by non-axial forces or the rod does not retract automatically, the rod will not interfere with proper placement of the plug.

Figure 31:
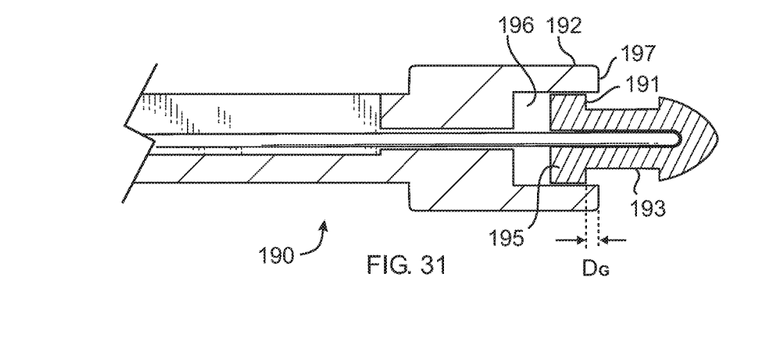
FIG. 31 is a diagrammatic partial cross-sectional side view of an alternate embodiment of the tool having a retractably carried plug in a mechanically unloaded condition with its cap fully recessed within the tool cup.

Referring now to FIG. 31 there is shown an alternate embodiment of the tool 190 similar to the tool of FIG. 28. However, in this embodiment the distal rim 197 of the coaxially oriented distal cup structure 192 is extended, and the internal cavity 196 made deeper so that while the tool is in its "at rest" state without an axial force applied, the punctal plug 193 is carried so that its cap 195 is fully contained in the cup. Thus, the distal rim 197 is located a distance DG axially distal from the distal flange surface 191 of the plug. In this embodiment there is always at least some amount of setback of the flange surface from the bearing surface so that over-insertion is prevented especially in those cases where the meatus is found to be overly dilated or otherwise looser than expected and the plug does not retract as expected when the axial force is applied.

Those skilled in the art of designing punctal plug inserters will readily recognize that some of the various features detailed in the various following embodiments can be utilized in an inserter shown using other features. For example, the cup structure of the embodiments of FIGS. 16 and 21 can use the compressible material of the embodiment of FIG. 25.

While the exemplary embodiments of the invention have been described, modifications can be made and other embodiments may be devised without departing from the spirit of the invention and the scope of the appended claims.

What is claimed is:

1. A tool for inserting a plug into the punctal opening of a meatus having a given diameter, wherein said plug comprises a body elongated along a first elongation axis, said body having a distal insertable portion, and a proximal cap having a distal flange surface oriented to rest against tissue surrounding said opening when said plug is positioned within said meatus;

wherein said tool comprises:
    a median member having a proximal portion, a distal portion, and an elongated tip projecting from said distal portion;
    a holder for releasably securing said plug to said tip;

said holder having a distal opening constantly large enough to allow axial passage of said proximal cap therethough, and at least one radial notch visibly exposing said cap while said plug is secured to said tip;

an insertion-resisting bearing surface located at an axial position coplanar with or distal to said flange surface when said plug is positioned within said meatus and said distal flange surface is resting against tissue surrounding said opening.

2. The tool of claim 1, wherein said holder comprises:
a radial prominence supporting said bearing surface axially spaced distally apart from said tip.

3. The tool of claim 2, wherein said at least one radial notch extends axially a first axial length.

4. The tool of claim 3, wherein said at least one radial notch extends angularly a first angle.

5. The tool of claim 2, wherein said at least one radial notch extends distally to an extent to form an angular discontinuity in said bearing surface.

6. The tool of claim 2, wherein said at least one radial notch has an outer opening larger than an inner opening.

7. The tool of claim 2, wherein said at least one radial notch is shaped and dimensioned to have a first angular dimension at a first axial location and a second angular dimension at a second axial location.

8. The tool of claim 2, which further comprises a pane of translucent material covering a portion of said notch.

9. The tool of claim 8, wherein said portion includes an entire angular and axial dimension of said notch.

10. The tool of claim 1, wherein said elongated tip projects along said first elongation axis along which the plug is ejected from said holder.

11. The tool of claim 1, wherein said holder has an insertion axis.

12. The tool of claim 11, wherein said insertion axis is oriented at an acute angle to said first elongation axis during insertion of said plug into said meatus.

13. The tool of claim 12, wherein said acute angle is between 0 and 45 degrees.

14. The tool of claim 1, wherein said holder comprises:
a cup terminating said tip and being axially aligned with said tip; and
wherein said cup has an internal geometry diametrically commensurate with said cap.

15. The tool of claim 14, wherein said cup is made from a resiliently flexible, translucent material.

16. The tool of claim 14, wherein said cup is removably securable to said tip.

17. The tool of claim 14, wherein said cap is spaced an axial distance apart from said cup.

18. The tool of claim 17, wherein said axial distance is eliminated when said plug is placed under a given axial mechanical load.

19. The tool of claim 1, wherein said insertable portion has a largest cross-diameter larger than said given diameter;
wherein said plug has an axial bore; and
wherein said tool further comprises a rod running axially within said tip and cup and having a distal extremity removably insertable into said bore.

20. The tool of claim 19, which further comprises a uni-directionally activated withdrawing mechanism housed in a cavity within said member; wherein said withdrawing mechanism is configured to manually cause withdrawal of said distal extremity from said cup.

21. The tool of claim 19, wherein said cap is spaced an axial distance apart from said cup; and wherein said axial distance is eliminated when said withdrawing mechanism activated.

22. The tool of claim 19, wherein said withdrawing mechanism comprises:
a movable beam within said cavity;
a pushbutton acting upon said beam; and
said rod having a proximal extremity secured to said beam.

23. The tool of claim 22, wherein said movable beam comprises a radially deflectable portion.

24. The tool of claim 22, wherein said movable beam comprises an axially translatable portion.

25. The tool of claim 22, wherein a distal extremity of said rod retracts axially under a given axial mechanical compression load.

26. A method for seating a plug in the punctum of a patient, wherein said plug has a proximal cap having a flange surface for resting against the tissue surrounding said punctum, said method comprises:
selecting an oblong inserter tool having a first end releasably carrying a punctal plug thereon, and a penetration-preventing bearing surface adjacent to a distal opening constantly large enough to allow axial passage of said proximal cap therethough;
pushing said tool axially until a contact is made between said bearing surface and a portion of tissue surrounding said punctum;
viewing said proximal cap during said pushing;
detecting an increase in resistance to further axial pushing while said contact is maintained;
stopping further axial pushing in response to said detecting;
releasing said plug from said tool; and,
axially pulling said tool away from said plug.

27. The method of claim 26, wherein said releasing comprises axially retracting a deformable rod from an axial bore in said plug.

28. The method of claim 26, which further comprises prior to said pushing, inserting a pre-sized dilator located on said tool into said punctum, wherein said dilator is dimensioned according to one of a plural number of sizes for said plug.

29. The method of claim 26, which further comprises:
carrying said plug where said flange surface is located in a first position an axial distance apart from said bearing surface;
and wherein said pushing comprises:
allowing said cap to retract proximally when said plug is placed under a given axial mechanical load, so that said axial distance is eliminated and said flange surface is located substantially coplanar with said bearing surface.

30. The method of claim 26, which further comprises:
carrying said plug where said flange surface is located in a first position an axial distance apart from said bearing surface;
and wherein said pushing comprises:
axially retracting a deformable rod from an axial bore in said plug thereby allowing said cap to retract proximally, so that said axial distance is eliminated and said flange surface is located substantially coplanar with said bearing surface.

31. The combination of a punctal plug and a tool for inserting said plug into the punctal opening of a meatus;
wherein said plug comprises:

a body elongated along a first axis;

a distal insertable portion;

a proximal cap having a distal flange surface oriented to rest against tissue surrounding said opening when said plug is properly emplaced in said meatus; and, wherein said tool comprises:

a median member having a proximal portion, a distal portion, and an elongated tip projecting from said distal portion;

a holder for releasably securing said plug to said tip;

said holder having a distal opening constantly large enough to allow axial passage of said proximal cap therethough; and, an insertion-resisting bearing surface located at an axial position to resist penetration of said flange surface through said punctum; and, at least one radial notch in said holder visibly exposing said distal flange surface while said plug is secured to said tip.

32. The combination of claim 31, wherein said bearing surface and said flange surface are substantially coplanar.

33. The combination of claim 31, wherein said holder comprises:

a cup terminating said tip and being axially aligned with said tip; and wherein said cup has an internal geometry commensurate with said cap.

34. The combination of claim 31, wherein said bearing surface continuously surrounds said flange surface.

35. The combination of claim 31, wherein said cap is retractably secured to said holder between an extended position and a retracted position and wherein said axial position is substantially coplanar with said distal flange surface when said cap is in said retracted position.

36. The combination of claim 31, wherein said combination further comprises:

said holder comprising a radial prominence supporting said insertion-resisting bearing surface.

37. The combination of claim 36, wherein said at least one radial notch extends axially a first axial length.

38. The combination of claim 37, wherein said at least one radial notch extends angularly a first angle.

39. The combination of claim 36, wherein said at least one radial notch extends distally to an extent to interrupt an angular gap in said bearing surface.

* * * * *